(12) United States Patent
Campbell et al.

(10) Patent No.: US 7,938,029 B2
(45) Date of Patent: May 10, 2011

(54) SIMPLIFIED OIL SAMPLING ASSEMBLY (76) Inventors: D. Michael Campbell, Lakeland, FL (US); Jack E. Zacks, Coral Gables, FL (US)

(*) Notice: Subject to any disclaimer, the term of this patent is extended or adjusted under 35 U.S.C. 154(b) by 440 days.

(21) Appl. No.: 11/590,164

(22) Filed: Oct. 31, 2006

(65) Prior Publication Data
US 2008/0098827 A1    May 1, 2008

(51) Int. Cl.
*G01N 1/14* (2006.01)
(52) U.S. Cl. .................. 73/864.34; 73/863.83
(58) Field of Classification Search ............ 73/863.71, 73/863.85, 863.81, 864.34
See application file for complete search history.

(56) References Cited

U.S. PATENT DOCUMENTS

| | | | |
|---|---|---|---|
| 3,974,659 A | 8/1976 | Edwards | |
| 4,378,026 A | 3/1983 | Bauer | |
| 4,484,482 A * | 11/1984 | Fournier et al. | 73/863.85 |
| 4,524,811 A | 6/1985 | Taylor | |
| 4,548,088 A | 10/1985 | Hood, Jr. | |
| 4,580,453 A * | 4/1986 | Taylor | 73/863.86 |
| 4,712,434 A * | 12/1987 | Herwig et al. | 73/864.63 |
| 4,864,877 A * | 9/1989 | Ortiz et al. | 73/863.52 |
| 4,925,627 A | 5/1990 | Johnson | |
| 5,265,483 A * | 11/1993 | Farrell et al. | 73/863.86 |
| 5,370,005 A * | 12/1994 | Fjerdingstad | 73/863.71 |
| 5,604,320 A * | 2/1997 | Boyd | 73/863.86 |
| 6,528,287 B2 | 3/2003 | Tomycz | |
| 7,082,848 B2 * | 8/2006 | Fjerdingstad | 73/863.85 |

* cited by examiner

*Primary Examiner* — Robert R Raevis
(74) *Attorney, Agent, or Firm* — Malloy & Malloy, P.A.

(57) ABSTRACT

An oil sampling assembly structured to collect an oil sample from the oil circulating system of an engine or other device and including a housing connected in fluid communication with the oil circulating system and having a container removably connected thereto. During operation of the oil circulating system a continuous flow of oil into and out of the container will occur. When the oil circulating system is not operating, oil and any contaminants contained therein will collect within the container. The container and oil sample is detached from the housing, replaced by another container, and connected to a closure for transport to a testing facility.

15 Claims, 4 Drawing Sheets

SIMPLIFIED OIL SAMPLING ASSEMBLY

BACKGROUND OF THE INVENTION

1. Field of the Invention

The present invention is directed to an oil sampling assembly wherein an oil sample and representative contaminants contained therein are collected within a container disposed in fluid communication with the oil circulating system of the engine or machinery being sampled. The container, once removed from its communicating relation with the oil circulating system is structured to define a shipping package for the transport of oil to a testing facility.

2. Description of the Related Art

The collection and testing of oil samples from engines, machinery, etc. are well known and intended to assure their efficient and long life operation by determining what contaminants exist within the oil circulating system. In preferred maintenance systems, oil sampling is conducted on a scheduled, predetermined, periodic basis and is a process by which a small amount of oil is extracted from the crank case, oil reservoir or other portion of the oil circulating system. Although the specified quantity of oil contained in an engine's oil reservoir generally varies, based on total cylinder displacement, this amount is generally far greater than that required to be collected as an oil sample for analysis. It is commonly recognized that an oil sample comprising generally 2-3 ounces is sufficient to perform a proper analysis as to contaminant content. Once collected, the oil sample is forwarded to an oil analysis lab or like testing facility to determine whether the contaminants found within the oil are expected to be present. If so, the levels of contamination are determined and compared with those levels known from prior sampling and those levels dictated by the manufacturer of the engine, machinery or like device being maintained.

When applying known or conventional techniques to obtain a representative oil sample, the engine or machinery is operated in a manner consistent with its design limits for a sufficient period of time to insure that the circulating oil reaches an operating temperature. Heating of the oil during circulation facilitates the evaporation of any water contained within the oil circulating system and further serves to sufficiently distribute any contaminants and other foreign substances consistently throughout the oil being circulated. After the aforementioned period of operation, the engine or machinery is shut down and a sufficient quantity of oil is removed from the oil reservoir or other appropriate portions of the oil circulating system. Such oil sample is typically transferred from the engine, machinery, etc. and placed into a suitable container for shipment to the oil analysis and/or testing facility.

Accordingly, problems and disadvantages associated with current, known or conventional oil sampling techniques include, among others, the necessity of operating an engine or machinery under normal operating conditions to ensure a complete heating of the oil within the circulating system of the engine or machinery to normal operating temperatures immediately preceding the collection of the oil samples for analysis. Sampling of oil at operating temperatures is not only difficult and inconvenient, using conventional procedures, but also can be dangerous in that normal operating oil temperatures can range from 190-220° F. Accordingly, the danger of coming into direct contact with hot oil in an attempt to remove small quantities thereof for sampling can result in serious damage to the sampler.

Additional disadvantages are associated with the conventional use of a suction pump or other extraction device used to remove the oil sampling from the crank case, oil reservoir, etc. When sampling oil from an I.C. engine, removal of the oil sample is frequently accomplished by inserting a thin hose or like conduit down through the dipstick tube and attaching the hose to some type of evacuation pump. The collected oil sample is thereby transferred while at potentially dangerous operating temperatures to a separate container. Thereafter the container containing the oil sample is transported, shipped, etc. to the analysis or testing facility.

It is recognized that advancements have been made in oil sampling techniques and attendant assemblies. By way of example only, diesel engine manufacturers sometimes build engines which incorporate oil sampling ports. This technique serves to eliminate the need to use a vacuum pump or like extraction device, as set forth above. Instead, access is made directly to the oil sampling ports for removal of the oil into an appropriate transport container for shipping. Therefore, while the engines incorporating sampling ports of the type set forth above may simplify and to a certain extent facilitate the process of obtaining hot oil samples, it does not eliminate the requirement of running the engine or machinery for a period of time to ensure the collected oil is at normal operating temperature. Other disadvantages associated with conventional oil sampling assemblies and procedures also lack the assurance that all contaminants are equally distributed throughout the oil being collected and/or circulated. A lack of consistent contaminant distribution throughout the oil circulating system may result in the collected oil sample not being accurately representative of the oil contained in the oil reservoir and/or oil circulating system in terms of contaminant content.

SUMMARY OF THE INVENTION

The present invention is directed to an oil sampling assembly structured to collect the oil sample from an oil reservoir or other appropriate portion of an oil circulating system of an engine, machinery or like device. As such, the sampling assembly of the present invention includes both structural and operative features intended to overcome problems and disadvantages associated with oil sampling assemblies, systems, techniques, etc. prevalent in existing technologies.

More specifically, the various preferred embodiments of the sampling assembly of the present invention facilitates the removal of an oil sample from the oil circulating system of engines, machinery, etc. without coming into direct contact with the oil. Further, after operation of the engine or machinery from which the sample is obtained, the oil may be allowed to cool to a temperature which is sufficiently low to eliminate or significantly reduce the possibilities of any damage being done to a user in the unlikely event of an inadvertent spill or contact between the oil sample and the individual taking the sample. Moreover, the collected oil sample will be representative, in terms of contained contaminants, of the oil circulating throughout the engine or machinery.

Accordingly, the present invention comprises a housing connected "inline" with the oil circulating system of the engine, machinery or like device from which the oil sample in obtained. Moreover, the housing includes an inlet assembly and an outlet assembly both connected in direct fluid communication to the oil circulating system. The sampling assembly of the present invention further includes a container removably connected to the housing. The container is dimensioned, configured and comprises an overall structure which facilitates the collection of an oil sample therein directly from the oil circulating system. Collection of the oil sample in a safe and efficient manner is facilitated by virtue of the fact that the interior of the container is also disposed in fluid communication with the oil circulating system through both the inlet-assembly and the outlet assembly of the housing.

Therefore, during operation of the engine or machinery the oil contained therein travels along the oil circulating system in the conventional fashion. However, due to the fluid interconnection between the sampling assembly and the oil circulating system, at least the housing and the container are connected to and at least partially define a path of fluid flow of the oil as it enters the inlet assembly, passes into the interior of the container and passes outwardly therefrom through the outlet assembly back into the normal path of travel of the oil circulating system. Therefore, it should be apparent that upon a shut down of the engine or machinery, the oil passing along the oil circulating system will eventually stop flowing, resulting in an oil sample being retained within the interior of the container. Moreover, the retained quantity of oil will include representative contaminants existing in the entire body of oil passing along the oil circulating system to and from a crank case, oil reservoir, etc.

Due to the fact that the container is removably connected to the housing in at least partially sealing engagement therewith, the collection of the oil sample retained within the interior of the container is accomplished by detachment of the container from the housing and the placement of a closure over the open end or other receiving portion of the container. In addition, the container and the closure are structured to define a package or shipping container which facilitates the transport, utilizing any conventional means, of the container and the collected oil sample to a testing or analysis facility for determination of the contaminants therein.

Moreover, when the container with a collected sample contained therein is detached from the housing and thereby removed from the oil circulating system, the present invention also contemplates the use of one or more replacement containers. Each replacement container may be equivalently structured to the original container described above. Upon removal of one container from the housing, as when an oil sample is being collected, another container is connected in operative relation to the housing as a replacement. This permits the continued operation of the engine or machinery being maintained as intended. As such, any one of a plurality of replacement containers is removably attached to the housing such that the aforementioned path of fluid flow is "closed" allowing the oil to continuously pass along the entire oil circulating system upon operation or activation of the engine or machinery.

Another advantage which further evidences the versatility of the present invention is the ability to eliminate "cross-contamination" between engines, such as when multiple engines are being sampled. More specifically, upon the removal of one container for purposes of sampling the oil retained therein, a new, replacement container may be substituted therefore. Such a replacement container may have been previously used and if so, the replacement container will be thoroughly cleaned so as to prevent any type of cross contamination. Such cross contamination is a possibility when containers are repeatedly used with different engines being sampled. Accordingly, either a replacement container, which has been cleaned, will be used upon the removal of an original container or alternatively a new, previously unused replacement container will be substituted therefore.

Therefore, certain disadvantages associated with conventional techniques and procedures for obtaining oil samples are overcome by virtue of collecting the oil sample within the container and not requiring it to be removed there from for purposes of transporting the oil sample to a testing facility. As a result the chance of contact or exposure of an individual to the collected oil is significantly reduced or eliminated. In addition once the engine or machinery being maintained has been shut down, the oil sample contained within the container may be allowed to cool before the container and the collected oil sample is removed from the housing. This further increases the safety factor in reducing the possibility of harm to the individual collecting the oil sample.

Another structural and operative feature of the sampling assembly of the present invention comprises the inclusion of a delivery device connected to the housing and directing oil flow from the inlet assembly directly to a predetermined contaminant collection portion on the interior of the container. More specifically, upon the shut down of the engine or machinery, oil within the interior of the container will come to rest resulting in a settling of any contaminants or other heavy material to a lower most portion of the container. This lower most portion may be more specifically described as the "contaminant collecting portion of the container." Further, the delivery device is disposed in direct fluid interconnection between the inlet assembly and the contaminant collection portion of the container.

In at least one preferred embodiment the delivery device includes an elongated delivery tube or conduit having one end connected to the housing in fluid communication with the inlet assembly and the opposite end defined by a delivery port disposed in direct fluid delivering relation to the contaminant collection portion of the container. Therefore when the engine or machinery is restarted, oil will flow from the oil circulating system directly through the elongated conduit of the delivery device and exit through the delivery port directly into the area which substantially defines the contaminant collecting portion. As such, any contaminants settling or collecting in this area will be distributed throughout the remaining oil within the container. Accordingly, the structural and operative features of the delivery device assure that any settled contaminants or other heavy material collected in the lower areas or other contaminant collecting portion of the container will be redistributed throughout the oil within the container each time a start-up of the engine or machinery occurs. Such contaminants will again flow back into the oil circulating system and become a part thereof. Continuous flow of oil through the aforementioned path of fluid flow, from the inlet assembly through the delivery device, into the interior of the container and back out through the outlet assembly, will assure a "fresh" oil sample being disposed within the container and having representative contaminants contained therein.

Moreover, when it is desired to remove an oil sample from the oil circulating system, the engine is shut down, the oil within the container may or may not be allowed to cool, the container is detached from the housing and thereby removed from the oil circulating system and a new replacement container is attached to the housing such that operation of the engine or machinery may continue. A closure is connected to the container in retaining, sealing relation to the collected oil sample. As such both the container and the attached closure may define a shipping package for transport of the collected oil sample to an analysis or testing facility to determine the scope of contaminants contained therein.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying drawings, the present invention is directed to a sampling assembly generally indicated as 10 which is adapted for collecting oil samples from engines, machinery, or other devices. As practically applied, the sampling assembly 10 is connected in fluid communication with an oil circulating system of the engine, machinery, etc.

Figure 3:
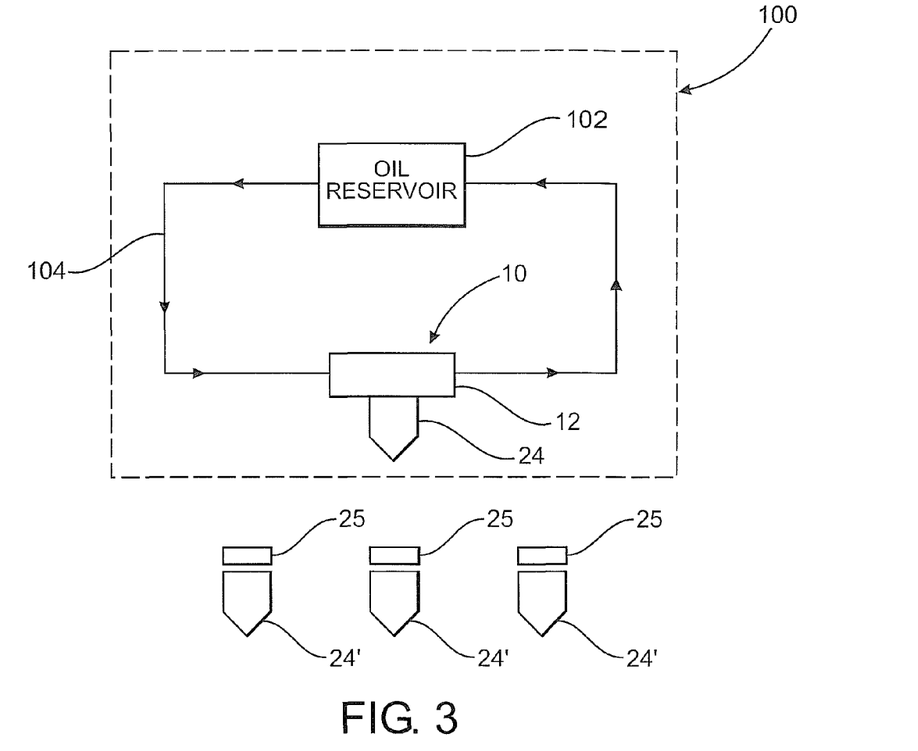
FIG. 3 is a schematic representation of an operative attachment of the sampling assembly of the present invention in fluid communication with an oil circulating system of an engine, machinery, etc.

As schematically represented in FIG. 3 and for purposes of clarity, the engine, machinery, etc. from which the oil sample is collected is generally indicated as 100 and includes a crankcase, oil reservoir or the like 102 as well as an oil circulating system 104. As schematically represented, the oil circulating system 104 defines the path of travel of the oil as it flows throughout appropriate and predetermined portions of the engine, machinery, etc. 100. As will be explained in greater detail hereinafter, the sampling assembly 10 is connected in fluid communication with the oil circulating system 104. As a result, a continuous flow of oil passes into and through the sampling assembly 10 during operation of the engine or machinery 100 due to continuous passage of oil along and throughout the oil circulating system 104.

Figure 1:
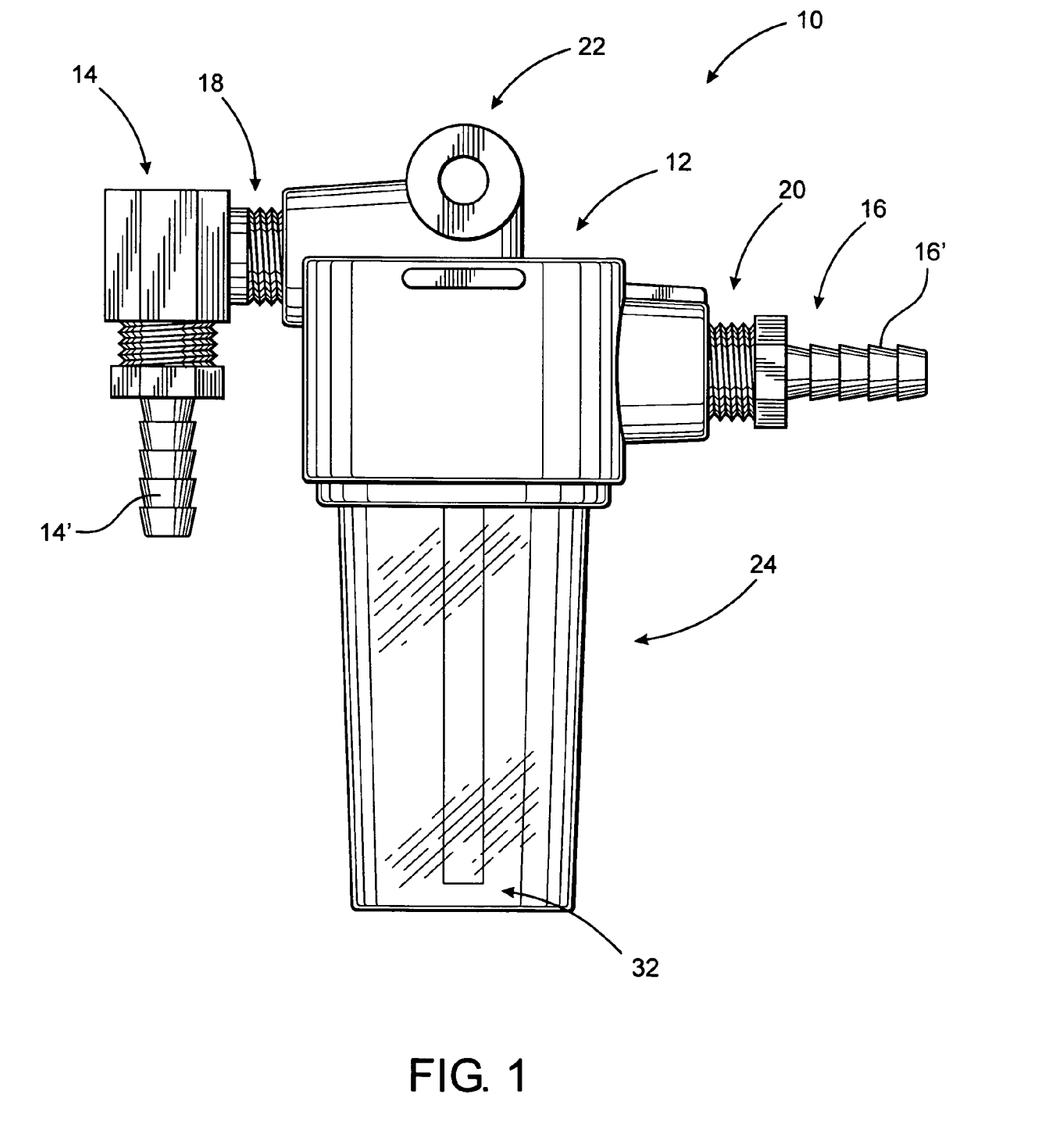
FIG. 1 is a front side view of at least one preferred embodiment of the sampling assembly of the present invention.
Figure 2:
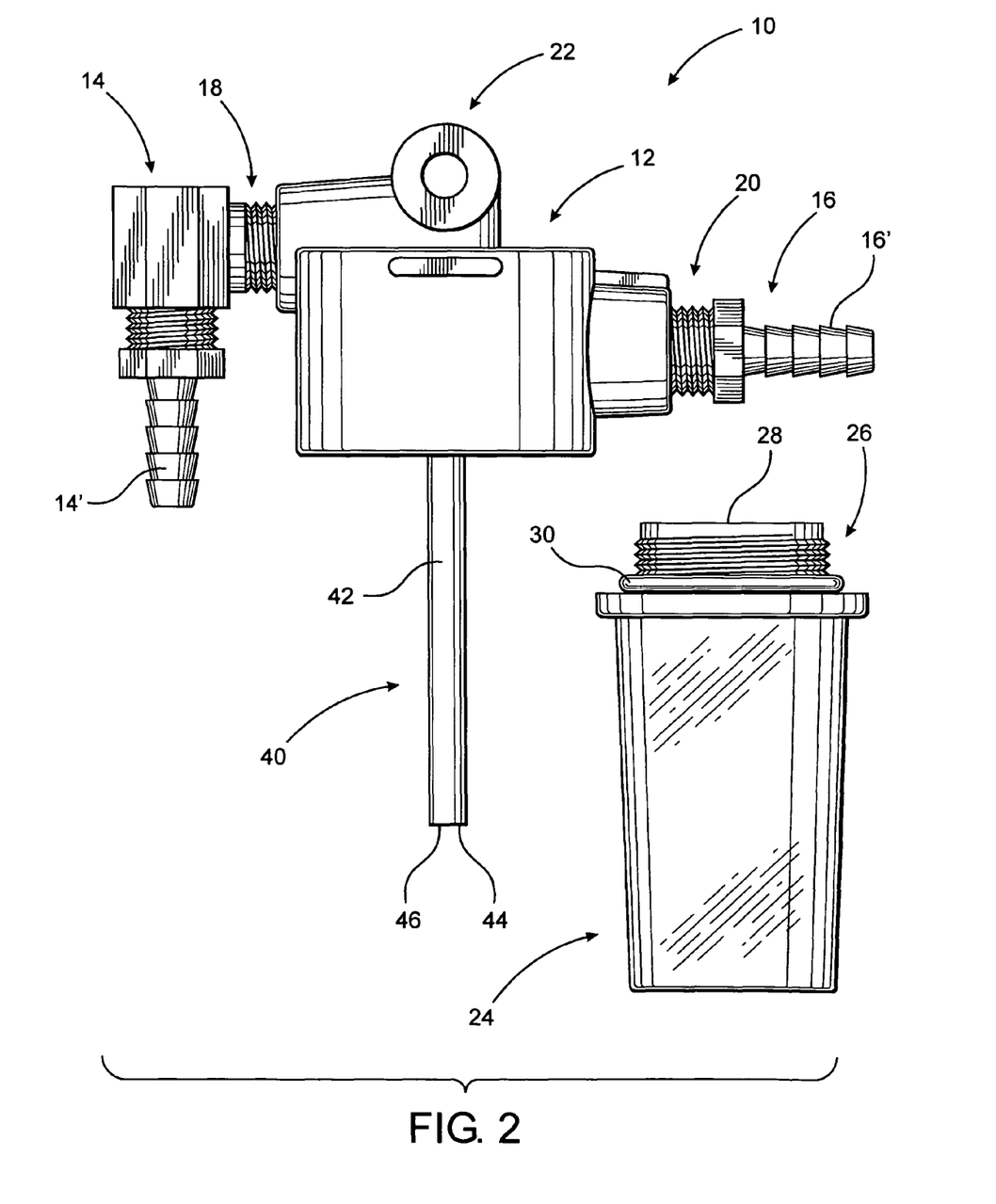
FIG. 2 is a front side view of the embodiment of FIG. 1 with a container of the sampling assembly being detached from a housing portion thereof.

With primary reference to FIGS. 1 and 2, the oil sampling assembly of the present invention comprises a housing generally indicated as 12. The housing 12 includes an inlet assembly 14 and an outlet assembly 16 both of which are connected in fluid communication with the oil circulating system 104 of the engine or machinery 100. The specific structural features of both the inlet assembly 14 and outlet assembly 16 may vary significantly such as by being removably or fixedly attached to the housing 12. In at least one preferred embodiment, as represented in FIG. 2, both the inlet assembly 14 and the outlet assembly 16 include inlet and outlet ports 14' and 16' respectively. The inlet and outlet assemblies 14 and 16 are structured to be appropriately connected to the oil circulating system 104, so as to facilitate the passage and flow of oil through the sampling system 10. In addition, the oil sampling assembly 10 may include a threaded interconnection as at 18 and 20 for the removable connection of the inlet assembly 14 and the outlet assembly 16 to the housing 12. Such removable connection while establishing a sealed path of fluid flow through sampling assembly 12 also facilitates the removal of the housing 12, inlet assembly 14 and/or the outlet assembly 16 for cleaning, replacement, repair, etc.

As set forth above, the present invention also contemplates either or both the inlet assembly 14 and the outlet assembly 16 being fixedly and/or integrally secured to the housing 12 if and when such a structural application is more appropriate to one or more specific practical applications. Other features which may or may not be included in the most preferred embodiment of the sampling assembly 10 include a mounting or connecting portion, generally indicated as 22, used to fixedly or removably secure the sampling assembly 10 in a stable, operative position as it is connected in fluid communication with the oil circulating system 104.

Additional structural and operative features of a most preferred embodiment of the present invention include the provision of a container generally indicated as 24. The container 24 has a hollow interior sufficiently dimensioned and configured to receive a sufficient quantity of oil therein to define an oil sample capable of being analyzed or tested using conventional and/or customized procedures. The container 24 is removably connected to the housing 12 when in its operative position represented in FIG. 1. Such a removable connection may be accomplished by a threaded configuration of the exterior periphery 26 of an open end 28 of the container 24. The threaded or other type connecting structure or configuration of the container 24 may correspond to a mating or connecting structure located on the interior of the housing 12 which is not shown for purposes of clarity. Therefore regardless of the specific mounting or connecting structure associated with both the container 24 and the housing 12, one feature of the of the present invention is the ability to detach the container 24, with an oil sample retained therein, from its operative position in fluid communication with the oil circulating system 104 via the inlet assembly 14 and the outlet assembly 16.

Moreover, this direct fluid connection with the oil circulating system 104 establishes a path of fluid flow of the oil through the sampling assembly 10, which is at least partially but more specifically defined by the inlet assembly 14, the housing 12, the interior of the container 24 and the outlet assembly 16. It should therefore be apparent that during operation of the engine or machinery 100, a continuous flow of oil will pass along the circulating system 104 and as such pass along the aforementioned and defined path of fluid flow through the sampling assembly 10 and into and out of the interior of the container 24. Accordingly, when the engine or machinery 100 is shut down the flow of oil along the oil circulating system 104 will stop, resulting in a collection or retention of a quantity of oil within the container 24. This retained oil may serve as an oil sample, which can be collected by the removal of the container 24 from the housing 12, as will be explained in greater detail hereinafter.

Other features associated with the container 24 include a seal structure 30 which may be in the form of an O-ring type seal or other seal structure which is disposed and/or compressed between the exterior surface of the container 24 in the area of the connecting or mounting structure 26 and the interior or appropriately adjacent portion of the housing 12. As such, continuous flow through the interior of the container 24 will not leak from the container 24 at the area of removable interconnection 26 between the container 24 and the housing 12. The seal structure 30 may also serve as a seal between the open end 28 of container and an attached closure 25 (see FIG. 3) when such a closure is secured in closing relation to the container 24 and retaining relation to an oil sample contained therein.

As generally discussed above, it is important that the collected oil sample contain representative contaminants which may be present in the oil flowing throughout the circulating system 104 and the oil reservoir 102 of the engine or machinery 100 being maintained and/or tested. As also set forth above, upon a shutting down of the engine or machinery 100 the oil continuously passing through the interior of the container 24 will be retained therein. During inactive periods of the engine or machinery 100, many contaminants and/or heavier solid materials may have a tendency to settle from a suspended orientation within oil and collect at a lower most or other collection region of the container 24. For purposes of clarity this region or area of collection is referred to herein as a "contaminant collecting portion" of the container 24 and is generally indicated as 32.

In order to avoid a "build-up" or surplus collection of such settled contaminants and/or particles within the contaminant collection portion 32, a most preferred embodiment of the present invention as represented in FIGS. 1 and 2 includes a delivery device generally indicated as 40. Delivery device 40 is disposed and structured to automatically remove or distribute any collected particles or contaminants having settled within the contaminant collection portion 32 of container 24 back throughout the oil maintained within the interior of the container 24 and eventually back into the oil circulating system 104. Therefore the oil sample collected within the interior of the container 24 will be a true representative of the contaminants contained within the entire oil circulating system 104 by the elimination of any accumulated build-up of settled contaminants from the interior of the container 24. Such removal of any settled contaminants or particles collected in the contaminant collection portion 32 will be accomplished each time the engine or machinery 100 is restarted for operation.

Accordingly, in at least one preferred embodiment of the present invention, the delivery device 40 comprises an elongated conduit 42 having one end fixedly or removably connected to the housing 12 in direct fluid receiving relation to the inlet assembly 14. Moreover, the elongated hollow interior conduit 42 has a length sufficient to extend into the interior of the container 24 such that a delivery port 46 located at a distal end 44 thereof is disposed in direct fluid delivering relation to the contaminant collecting portion 32.

Accordingly, the delivery device 40 may be considered a part of the inlet assembly 14 or may be considered as a separate but cooperatively disposed component. In either structural modification, the delivery conduit 42 is disposed and structured to direct oil flowing from the oil circulating assembly 104 into the housing 12 through the inlet assembly 14, directly to the contaminant collecting portion 32 of the container 24. Such a specifically directed flow of oil from the delivery conduit 42 is accomplished by having its opposite or distal end 44 being structured to include the delivery port 46. The delivery port 46 is disposed to direct a forced flow of oil, provided by the oil circulating system 104, directly on to the contaminant collection area 32. The force of the incoming oil exiting the delivery port 46 is sufficient to cause a "flushing" of the contaminants or particles which may have accumulated in the contaminant collecting portion 32 and a distribution thereof throughout the remaining quantity of oil contained within the interior of the container 24. The distributed contaminants will eventually flow through the outlet assembly 16 back into the oil circulating system 104, each time the engine or machinery 100 is activated or becomes operational.

When it is desired to collect an oil sample for analysis and/or testing, the engine or machinery 100 is initially allowed to run for an operational cycle which is sufficient in length and load to cause the engine or machinery and all fluids circulating therethrough to reach normal operational temperatures. During this operational cycle and as set forth above, oil from the circulating system 104 will continuously pass along the aforementioned path of fluid flow, through the sampling assembly 10 and into and out of the interior of the container 24. Once the engine or machinery 100 is shut down after the operational cycle is been completed, oil will remain within the interior of the container 24. This retained oil will define an oil sample having a representative amount of contaminants therein, as explained above. Collecting the sample involves detachment of the container 24 from the housing 12 in the manner generally shown in FIG. 2 and a replacement of one or more replacement containers 24' (see FIG. 3) back into the operational position represented in FIGS. 1 and 3. Upon detachment of the container 24, the oil sample will be retained and sealed therein through the connection of a closure 25 in sealing relation to the open end 28 of the container 24. Both the container 24 and the closure 25 will thereby define a package or shipping container which is structured to transport the oil sample sealed and retained within the interior of the container 24 to an appropriate analysis and testing facility for determination of contaminant scope contained therein.

Figure 4:
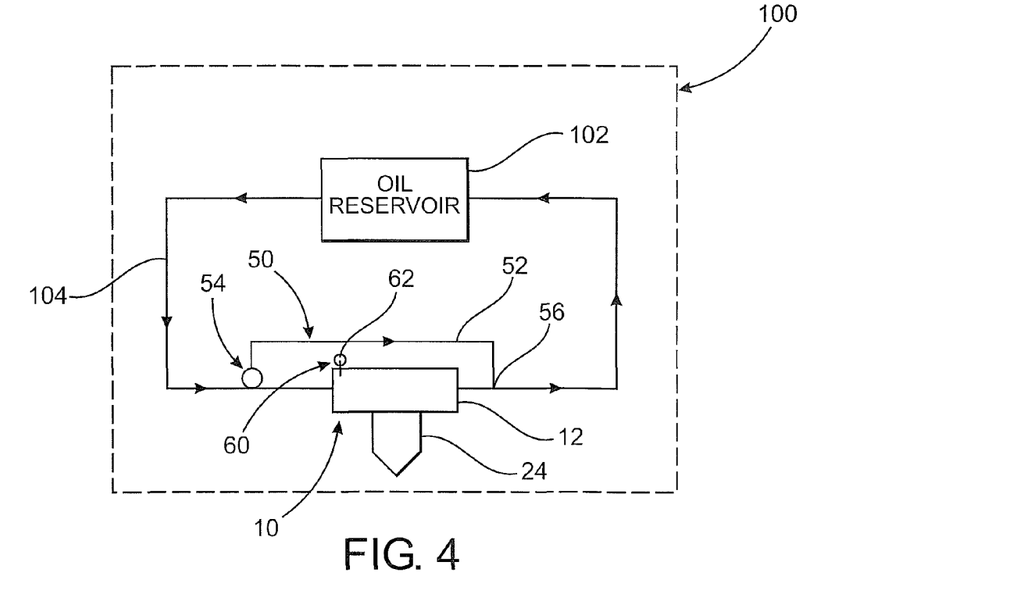
FIG. 4 is a schematic representation of another preferred embodiment of the present invention, wherein a bypass assembly may be incorporated with the sampling assembly and the circulating system of the engine being sampled.

Yet another preferred embodiment of the present invention is represented in FIG. 4 and includes structural modifications and/or additions which facilitate the efficient operation of the sampling assembly 10 in conjunction with its direct fluid communication with the oil circulating system 104 of the engine or machinery 100 being sampled. More specifically, a bypass assembly is generally indicated as 50 and includes a bypass line 52 which is connected to the oil circulating system 104 and removed from direct fluid communication with the sampling assembly 10. As represented, the bypass line 52 is disposed and structured to direct the flow of oil in a manner which will bypass the sampling assembly 10. In addition, the bypass assembly 50 further includes at least one valve structure 54 connected in fluid communication with the oil circulating system 104 and the bypass line or conduit 52.

When activated or operated in its intended manner, the valve structure 54 serves to direct oil flowing through the oil circulating system 104 into and through the bypass conduit 52 in a manner which will prevent oil flowing into and/or through the sampling assembly 10. As clearly represented in FIG. 4, the bypass line or conduit 52 is connected, preferably at a distal end or portion thereof 56, in direct fluid communication with the oil circulating system 104 "downstream" of the sampling assembly 10. As such, oil will continue to flow through out the engine 100 being sampled for purposes of cooling and/or lubricating intended operating components of the engine and/or machinery 100. Accordingly, the provision of a bypass assembly 50 allows an individual to obtain oil samples by removing and replacing one or more containers 24, in the manner described above, during a continuous operation of the engine or machinery 100.

In order to facilitate the collection of the oil to be sampled from the oil sampling assembly 10 by removal of the container 24, another structural modification, representative of yet another preferred embodiment of the present invention, is the provision of an intake assembly generally indicated as 60. Intake assembly 60 includes an intake valve, vent, port, etc. which is preferably selectively operable. The intake assembly 60 is disposed at an appropriate location, relative to both the inlet assembly 14 and the remaining components of the sampling assembly 10, and structured to allow the in-flow of air, or other fluid, into the sampling assembly 10. Moreover, the incoming air is directed through an "air break device" 62 from an exterior of the housing 12 into the interior of a container 24 connected to the housing 12. As a result, operation of the intake assembly 60 and air break device 62 serves to displace oil which would normally be retained within the container 24 and force it back into the oil circulating system 104. The level and volume of retained oil within the container 24 is thereby reduced. A lower volume and level of oil will facilitate the removal of the container 24 and retained oil sample therein in a manner which eliminates or significantly reduces spillage. In turn, a reduced possibility of spillage further reduces the possibility of the oil sample coming into direct contact with an individual. It should be apparent that the specific structure, location and operation of the intake assembly 60 and/or air break device 62 may vary such that air will be directed into the interior of the container 24 in an effective and efficient manner so as to appropriately reduce the volume of oil which would normally be retained within the container 24 for the reasons set forth above.

Figure 5:
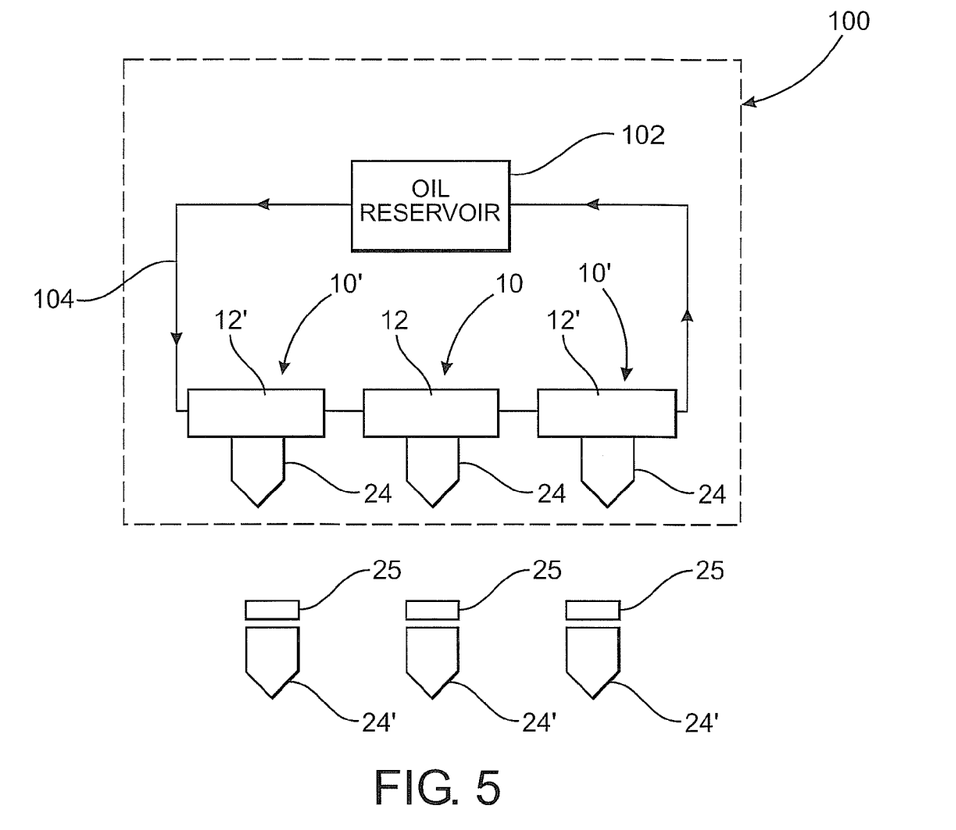
FIG. 5 is yet another preferred embodiment of the present invention, wherein a plurality of sampling assemblies may be operatively positioned in series such that any each of a plurality of containers and/or replacement containers may retain oil samples removed from the oil circulating system of the engine being sampled.

FIG. 5 is representative of yet another preferred embodiment of the present invention wherein a plurality of oil sampling assemblies 10 and 10' are located sequentially in series. As such, each of the plurality of sampling assemblies 10 and 10' are connected in direct fluid communication with the oil circulating system 104. The oil being sampled may be removed from the oil circulating system 104 by removal of any one of the plurality of containers 24. When so removed, a replacement container 24' may be substituted therefore as explained in detail above. Further, the sampling containers 10 and 10' are connected in direct fluid communication with the oil circulating system 104. Accordingly, an individual can collect an oil sample from any one or all of the oil containers 24 and/or may sample the oil from alternative ones of the plurality of containers 24 so as to assure the accuracy of the contaminant level throughout the oil circulating system 104.

For purposes of clarity FIG. 5 is a schematic representation of the plurality of sampling assemblies 10 and 10' located substantially sequentially and in series relative to one another. However, the present invention also contemplates each of the sampling assemblies 10 and 10' being located at a variety of different locations, wherein the sampling assemblies 10 and 10' may be at least a minimally remote from one another throughout the oil circulating system 104. Further, while at least one preferred embodiment of the present invention has the plurality of sampling assemblies 10 and 10' located in series with one another, it is also contemplated to be within the spirit and scope of the present invention to have one or more of the plurality of sampling assemblies 10 or 10' located in different parts such that a "series" flow of oil being sampled is avoided.

As also should be apparent, it is emphasized that each of the sampling assemblies 10 or 10' as represented in FIG. 5, includes the above described delivery device 40 including independent, an elongated conduit 42 having one end fixedly or removably connected to a corresponding housing 12 in direct fluid receiving relation to a corresponding inlet assembly 14. Further, the length of each of the corresponding ones of the conduits 42 is sufficient to extend into the interior of the respective containers 24, such that a delivery port 46 is disposed in direct fluid delivery relation to a contaminant collecting portion 32 as explained in detail with primary reference to FIGS. 1 and 2. As such, each delivery device 40 associated with different ones of sampling assemblies 10 and 10' are disposed and structured to remove or distribute any collected particles or contaminants which have settled within the respective ones of the contaminant collection portions 32 of the corresponding containers 24.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A sampling assembly structured to collect an oil sample from an oil circulating system, said assembly comprising:
    a housing including an inlet assembly and an outlet assembly,
    at least one container removably connected to said housing and including an interior,
    said interior connected in continuous fluid communication with oil circulating system through said inlet assembly and said outlet assembly and disposed and structured to collect an oil sample therein when connected to said housing when the circulating system is not operating,
    a delivery device disposed and structured to distribute contaminants collected within said container substantially throughout said interior and the oil contained therein, and
    said housing and said container connected in fluid communication to and at least partially defining an unrestricted path of fluid flow of the oil circulating system,
    said unrestricted path of fluid flow comprising a continuous passage of oil from said inlet assembly through said delivery device, into said interior of said container and therefrom out through said outlet assembly during continuous operation of the oil circulating system, and
    said housing and said container cooperatively structured to remove the oil sample from said unrestricted path of fluid flow by disconnection of said container from said housing when the oil circulating system is not operating.

2. A sampling assembly as recited in claim 1 wherein said container is structured to contain and transport the collected oil sample for testing.

3. A sampling assembly as recited in claim 1 wherein said container comprises a contaminant collecting portion at least partially defined by an area within said interior in which contaminants settle during inoperative periods of the oil circulating system.

4. A sampling assembly as recited in claim 3 wherein said delivery device is disposed and structured to direct oil from said unrestricted path of fluid flow substantially directly to said contaminant collecting portion.

5. A sampling assembly as recited in claim 4 wherein said delivery device comprises a conduit connected to said housing and including a delivery port disposed in direct fluid delivering relation to said contaminant collecting portion.

6. A sampling assembly as recited in claim 5 wherein said conduit comprises an elongated configuration having one end connected to said housing, said delivery port disposed at an opposite end of said conduit.

7. A sampling assembly as recited in claim 6 wherein at least a majority of the length of said conduit is disposed within said interior when said container when said container is connected to said housing.

8. A sampling assembly structured to collect oil samples from an oil circulating system, said assembly comprising:
    a housing including an inlet assembly and an outlet assembly disposed in fluid communication with the oil circulating system,
    at least one container removably connected to said housing and disposed in fluid communication with the oil circulating system via said inlet assembly and said outlet assembly, said container structured to collect an oil sample therein when connected to said housing and including a contaminant collection portion on an interior of said container, a delivery device at least partially disposed within said container and structured to direct oil from said inlet assembly substantially directly to said contaminant collection portion, an unrestricted path of fluid flow communicating with the oil circulating system and comprising a continuous passage of oil from said inlet assembly, through said delivery device, into said interior of said container, and therefrom out through said outlet assembly during continuous operation of the oil circulating system, said housing and said container being cooperatively structured to remove the oil sample from the oil circulating system by disconnection of said container from said housing upon discontinued operation of the oil circulating system, and an intake assembly disposed in fluid communication between an exterior of said housing and an interior of said one container, said intake assembly including an air break structured to selectively increase a volume of air and correspondingly reduce the volume of oil within said interior of said container, wherein the reduced volume of oil is sufficient to facilitate removal of said container from said housing without spillage of the retained oil therein.

9. An oil sampling assembly as recited in claim 8 wherein said container is structured to contain and transport the collected oil sample for testing.

10. An oil sampling assembly as recited in claim 8 wherein said delivery device comprises a conduit a delivery port disposed at a distal end thereof, said conduit being of a sufficient length to extend along at least a majority of said interior of said container for disposition of said delivery port in direct fluid delivering relation to said containment collection portion.

11. A sampling assembly as recited in claim 10 wherein at least a majority of the length of said conduit is disposed within said interior of said container when said container is connected to said housing.

12. A sampling assembly as recited in claim 8 further comprising a bypass assembly selectively connected in continuous fluid communication with the oil circulating system and disposed and structured to selectively bypass said housing and said container connected to said housing concurrent to establishing a continuous flow of oil through the oil circulating system during the operation of the oil circulation system.

13. A sampling assembly as recited in claim 12 wherein said bypass assembly includes a valve structure connected upstream of said housing along the oil circulating system, said valve structure disposed and structured to direct fluid flow from a location upstream of said housing to a location downstream of said housing and in bypassing relation to said housing.

14. An assembly structured to collect oil samples from an oil circulating system, said assembly comprising:

a plurality of housings each including an inlet assembly and an outlet assembly disposed in fluid communication with the oil circulating system, a plurality of containers each removably connected to a different one of said plurality of housings and disposed in fluid communication with the oil circulating system via corresponding ones of said inlet assembly and said outlet assembly, each of said containers structured to collect an independent oil sample therein when connected to corresponding ones of said housings, each of said containers including a contaminant collection portion on an interior thereof, a plurality of delivery devices each at least partially disposed within a different one of said containers, each of said delivery devices structured to direct oil from a corresponding one of said inlet assemblies substantially directly to corresponding ones of said contaminant collection portions, a path of fluid flow communicating with the oil circulating system and comprising a passage of oil from each of said inlet assemblies through respective ones of said delivery devices, into said interior of corresponding ones of said containers and therefrom out through corresponding ones of said outflow assemblies during operation of the oil circulating system, and each of said housings and corresponding ones of said containers being cooperatively structured to remove different oil sample from the oil circulating system by disconnection of respective ones of said containers from corresponding ones of said housings.

15. An assembly as recited in claim 14 wherein each of said containers is structured to at least partially define a package, each of said packages structured to transport a collected oil sample for testing.

* * * * *